United States Patent
Rosengaus

(10) Patent No.: US 7,724,362 B1
(45) Date of Patent: May 25, 2010

(54) OBLIQUE INCIDENCE MACRO WAFER INSPECTION

(75) Inventor: Eliezer Rosengaus, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 318 days.

(21) Appl. No.: 11/715,804

(22) Filed: Mar. 8, 2007

Related U.S. Application Data

(60) Provisional application No. 60/782,048, filed on Mar. 14, 2006.

(51) Int. Cl.
*G01N 21/00* (2006.01)

(52) U.S. Cl. .................. 356/237.4; 356/237.5

(58) Field of Classification Search ... 356/237.1–237.5, 356/369
See application file for complete search history.

(56) References Cited

U.S. PATENT DOCUMENTS

| | | | | |
|---|---|---|---|---|
| 4,966,457 A * | 10/1990 | Hayano et al. | ........... | 356/239.7 |
| 5,106,196 A * | 4/1992 | Brierley | ....................... | 356/445 |
| 5,777,729 A | 7/1998 | Aiyer et al. | ............... | 356/237.1 |
| 5,917,588 A * | 6/1999 | Addiego | ................... | 356/237.2 |
| 6,128,093 A * | 10/2000 | Niikura | ....................... | 356/432 |
| 6,603,542 B1 * | 8/2003 | Chase et al. | ............. | 356/237.4 |
| 6,630,996 B2 * | 10/2003 | Rao et al. | ................. | 356/237.5 |
| 7,142,300 B2 | 11/2006 | Rosengaus | ................... | 356/369 |
| 7,292,341 B2 * | 11/2007 | Brill et al. | .................... | 356/445 |
| 2005/0094864 A1 * | 5/2005 | Xu et al. | ...................... | 382/145 |

* cited by examiner

*Primary Examiner*—Hoa Q Pham

(57) ABSTRACT

A line image acquisition apparatus suitable for being added onto a line-scan wafer macro-inspection system which incorporates oblique incidence illumination and detection, both for brightfield and for darkfield, which incorporates double darkfield observation capability, which incorporates broadly tunable angle of incidence illumination and tunable angle of detection, which incorporates multi-channel detection into a line-scan macro-inspection system, and which is an add-on feature compatible with current line-scan macro-inspection systems.

34 Claims, 9 Drawing Sheets

OBLIQUE INCIDENCE MACRO WAFER INSPECTION

CROSS REFERENCE TO RELATED APPLICATIONS

This application corresponds to US Provisional Application No. 60/782,048, filed Mar. 14, 2006, and claims priority therefrom.

FIELD OF THE INVENTION

This invention relates to integrated circuit technology, and in particular to macro inspection of integrated circuit wafers.

BACKGROUND OF THE INVENTION

When performing macro inspection of integrated circuit wafers, several factors contribute to its effectiveness under varying circumstances. Included among these factors are the illumination angle, illumination intensity, angle of detection, polarization. The illumination and detection angles in particular affect observation in many ways. Brightfield observation occurs when the detected light is specularly reflected from the sample surface, i.e., when the angle of illumination and the angle of detection are the same. Brightfield inspection is useful for inspecting patterned regions with shallow topography, i.e., not much z variation. On the other hand, dark field inspection detects scattered and diffracted light, rather than specularly reflected light. Dark field inspection is often more effective when small changes are being detected, since a small change causes a larger percentage change of the less intense scattered darkfield signal.

In the case of integrated circuit inspection, the metal lines on the circuit in general approximate a grating configuration, so that scattered light usually forms a diffraction pattern. The grating equation applies:

$$\sin(\theta) + \sin(\theta_i) = n\lambda/D$$

where $\lambda$, is the wavelength of incident light, D is the grating spacing, $\theta_i$ is the angle of incidence of light with respect to a surface normal, $\theta$ is the angle of detection of light, and n is the diffraction order. FIG. 1a illustrates a resulting diffraction pattern in side view. Incident light beam 100 from illumination source 105 is at angle $\theta_i$ from normal onto sample 110. Zeroeth order diffracted light beam 115, i.e., specularly reflected beam is shown at angle $\theta_i$, as well as first order diffracted beam 120 centered at angle $\theta_1$ and second order diffracted beam 125 centered at angle $\theta_2$. The diffracted beams can be thought of as narrow "lobes" centered at the respective angles. The lobes typically decrease in intensity as the diffraction order increases. For detecting small changes in the sample structure, e.g. defocus effects, it is preferable to observe the higher order diffraction lobes, which will show the largest percentage change.

As the grating spacing D decreases, i.e. integrated circuit dimensions decrease and packing density increases, the diffraction lobes separate and spread out. As D approaches $\lambda$, it is necessary to have a larger angle of incidence in order to see higher order diffraction lobes. Also, the higher order diffraction lobes will appear at larger angles away from normal as D decreases, therefore the detection angle must also increase. This can be demonstrated as follows:

Assume that $D=2\lambda$, and assume normal incidence light, i.e., $\theta_i=0$. Then the grating equation becomes $\sin(\theta)+\sin(0)=n/2$, or $\sin(\theta)=n/2$. In this case, shown in FIG. 1b, the first order diffraction lobe 130 (n=1) will be centered at a 30 degree angle from normal to the sample surface, and the second order diffraction lobe 135 will extend parallel to the sample surface, nearly impossible to detect. Assuming grazing incidence light, i.e., $\theta_i=90$ degrees, then the grating equation becomes $\sin(\theta)+\sin(90)=n/2$, or $\sin(\theta)=n/2-1$. In this case, shown in FIG. 1c, the first order diffraction lobe 140 will be at a −30 degree angle from normal to the surface, (i.e., in the same quadrant as the incident light), the second order diffraction lobe 145 will be normal to the surface, the third order diffraction lobe 150 will be at a +30 degree angle from normal, and the fourth order diffraction lobe 155 will extend parallel to the sample surface.

Clearly, then, using oblique incidence light, and being able to tune the angle of detection to be a variable off-normal angle, yield advantages for darkfield sample inspection when higher order diffraction lobes are preferable, as in the case when inspecting for defocus defects. The ability to vary both the angle of incidence and angle of detection of light would provide the maximum flexibility to optimize inspection according to the details of the sample. The use of oblique incidence additionally yields a strong polarization dependence which is not present for normal incidence light. This polarization dependence, which increases as the angle of incidence increases away from normal, is further described in commonly authored and owned U.S. patent application Ser. No. 10/829,727, filed Apr. 22, 2004, issued as U.S. Pat. No. 7,142,300, on Nov. 28, 2006, which is hereby incorporated by reference. This effect provides substantial background suppression, allowing improved inspection of small changes in signal.

A manual inspection system incorporating a tiltable, rotatable table for mounting the sample on so as to provide a wide range of incidence angles for brightfield inspection is described in U.S. Pat. No. 5,096,291, issued Mar. 17, 1992. An inspection system using diffracted light is described in U.S. Pat. No. 5,777,729 (assigned to Nikon Corp.), issued Jul. 7, 1998. As described therein, (and as implemented in the Nikon AMI inspection system), the wafer to be inspected is mounted on a tiltable, rotatable plate so as to be able to tune the inspection angle. The wafer motion during inspection causes problems in matching images. Furthermore, the large parabolic mirrors used for collecting outgoing light have a large focal length, resulting in a very large inspection machine, which costs valuable fab space.

An extension of darkfield detection known as "double darkfield" occurs when the incident light beam and the scattered beam which is detected are not co-planar. In the most pronounced case, illustrated in FIG. 2, the xz plane 205 formed by the incident beam 210 and the sample normal 212 is perpendicular to the yz plane 215 formed by the detected scattered beam 220 (by detector 225) and the sample normal. In this case, the detected light has been scattered in two directions, which provides for a very low background intensity upon which small changes are quite pronounced.

A method of incorporating oblique incidence illumination and double darkfield capability, as well as broad tunability of angle of incidence and angle of detection, into a line scan macro-inspection system such as the Viper system by KLA-Tencor (described in U.S. Pat. No. 5,917,588 by Addiego, which is hereby incorporated by reference), would be a significant advancement in macro-inspection technology. (The current Viper system has limited oblique incidence and detection for brightfield, but with angle limited to being fairly close to normal, i.e., approximately + or −30 degrees, so as to not interfere with the motion stage). The additional ability to incorporate multi-channel detection would allow the most complete inspection according to multiple parameter variations.

SUMMARY OF THE INVENTION

It is therefore an object of this invention to provide a method and apparatus for incorporating oblique incidence illumination and detection, both for brightfield and for darkfield, into a macro-inspection system such as a line-scan macro-inspection system.

It is a further object of this invention to provide a method and apparatus for incorporating double darkfield observation capability into a macro-inspection system such as a line-scan macro-inspection system.

It is a further object of this invention to provide a method and apparatus for incorporating broadly tunable angle of incidence illumination and tunable angle of detection into a macro-inspection system such as a line-scan macro-inspection system.

It is a further object of this invention to provide a method and apparatus for incorporating multi-channel detection into a macro-inspection system such as a line-scan macro-inspection system.

It is a further object of this invention to provide the above-mentioned improvements to a line-scan macro-inspection system as an add-on feature which is compatible with current line-scan macro-inspection systems.

These objects are met by the method and apparatus disclosed herein.

DETAILED DESCRIPTION OF THE INVENTION

Figure 1A:
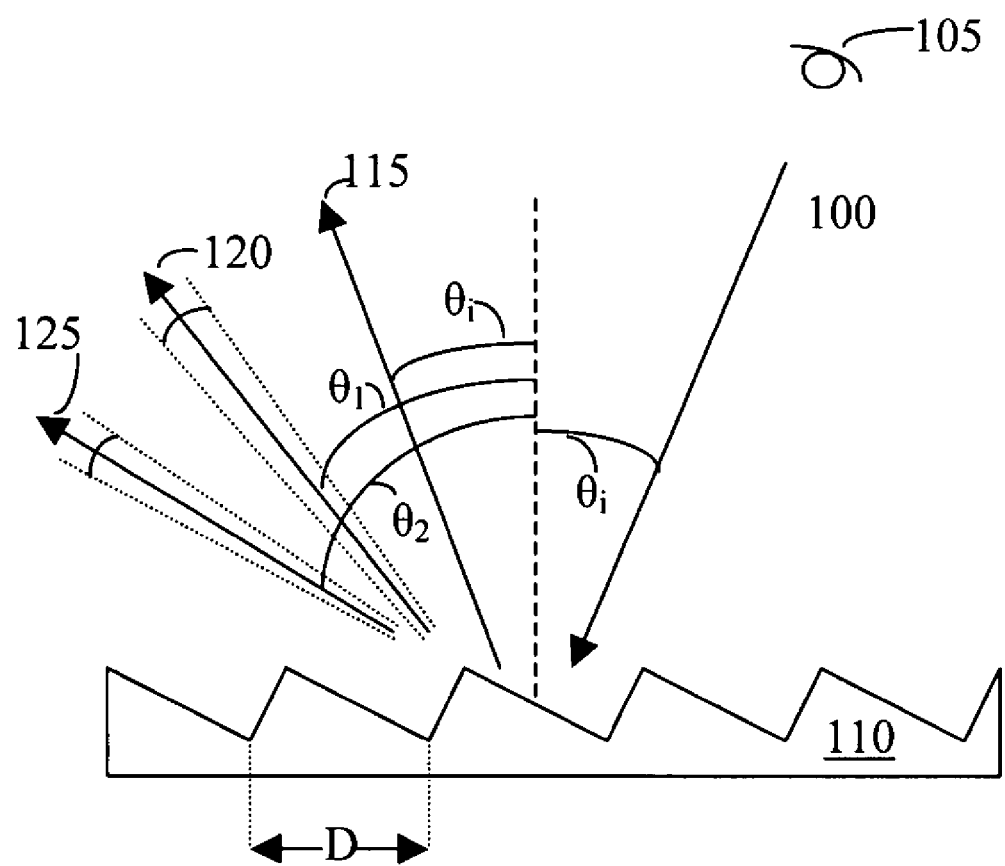
FIG. 1a shows a side view of diffracted rays from a diffraction grating.
Figure 1B:
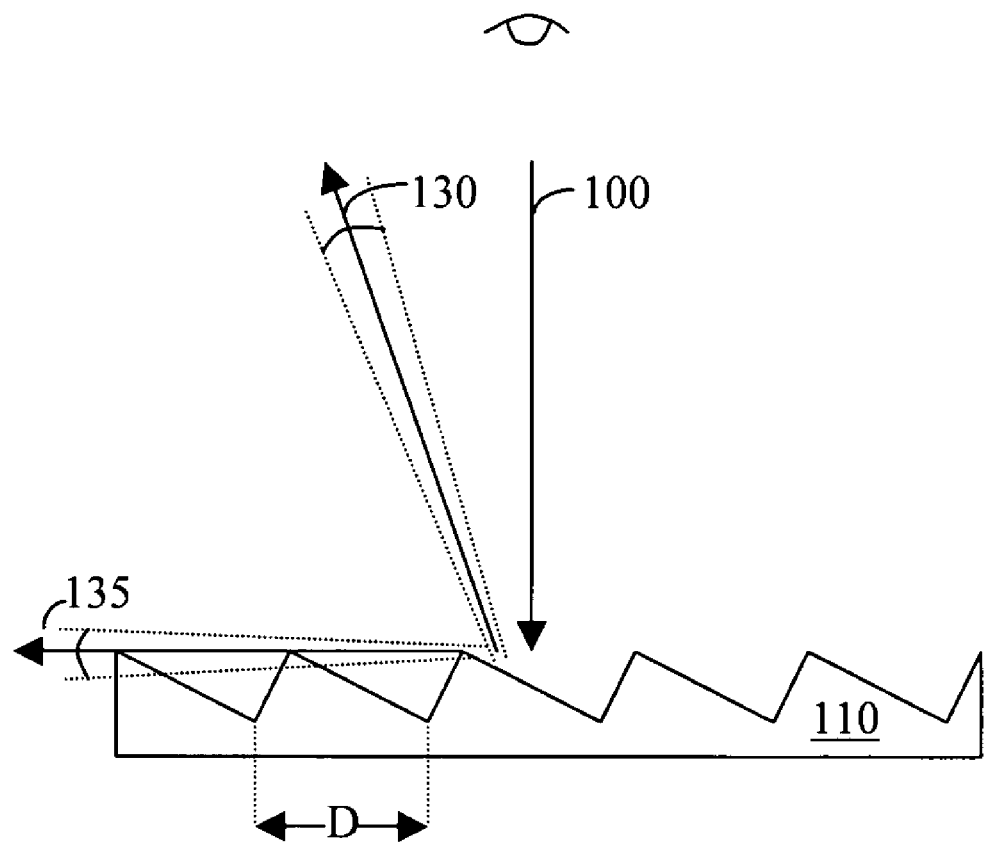
FIG. 1b shows the diffracted rays for normal incidence light when $\lambda=D$.
Figure 1C:
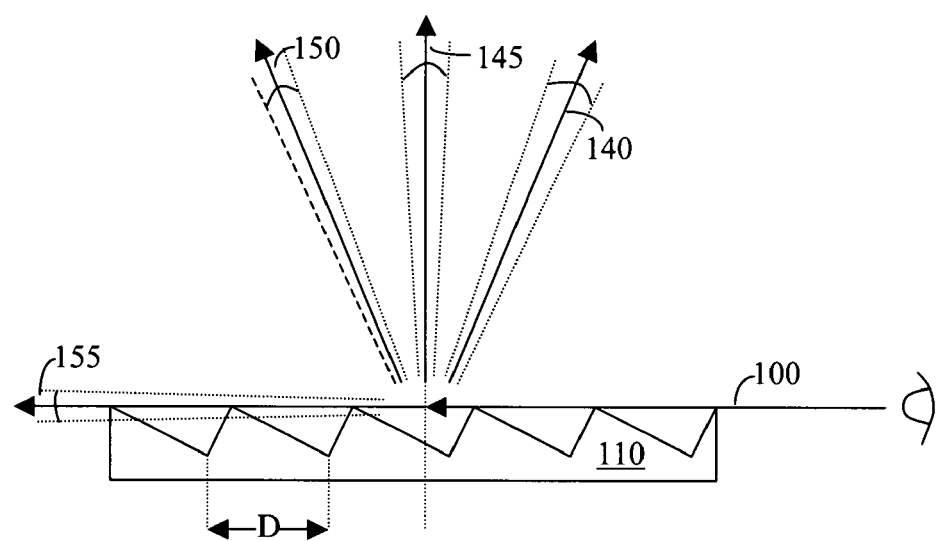
FIG. 1c shows the diffracted rays for grazing incidence light when $\lambda=D$.
Figure 2:
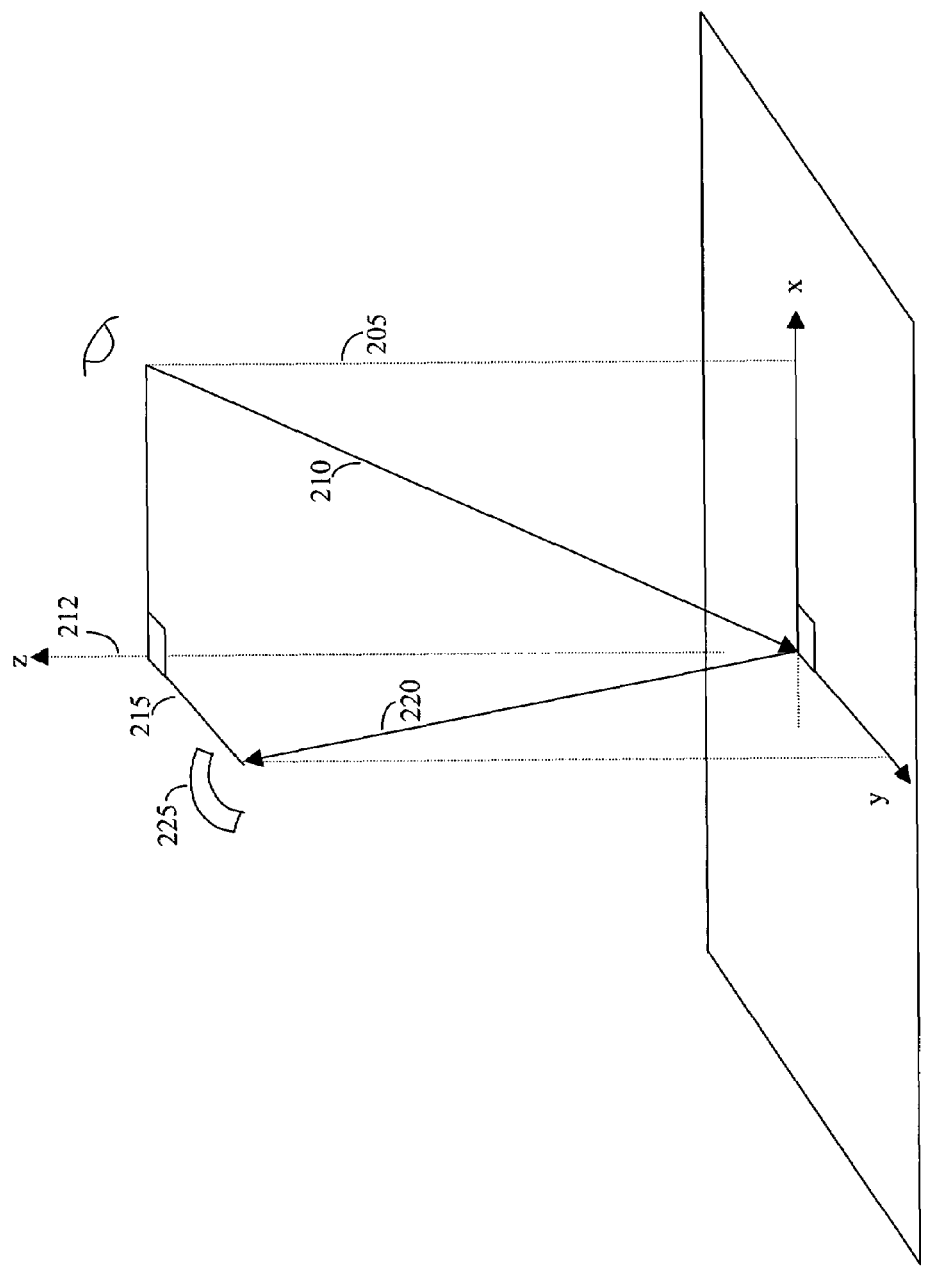
FIG. 2 illustrates double-darkfield detection.
Figure 3:
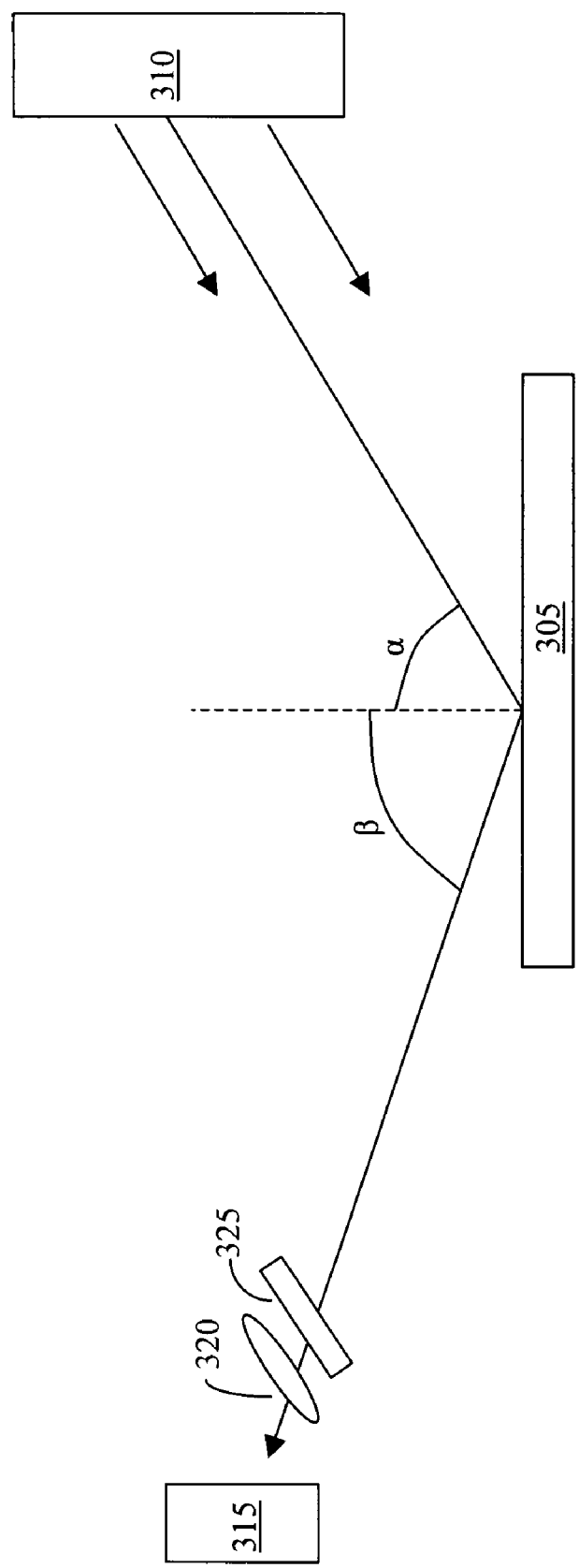
FIG. 3 shows a configuration used to test the sensitivity of defocus defects to detection under oblique incidence illumination, using a two dimensional detector.

FIG. 3 shows a configuration used to test the sensitivity of defocus defects to detection under oblique incidence illumination. Sample 305 is illuminated from oblique angle α by illuminator 310, which is shown in this case to be a fluorescent light box. The light box has a heavy diffuser in front of the fluorescent tubes to provide uniform, diffuse illumination. The spectrum of the fluorescent illuminator consists primarily of the narrow spectral lines of Hg. Detector 315 is a conventional 2-dimensional color camera, in this case a commercial SLR Digital camera. The lens 320 and the detector 315 are tilted with respect to the sample surface according to the Scheimpflug configuration which allows the sample to stay in focus across the sample with oblique incidence illumination. The Scheimpflug geometry is discussed in U.S. Pat. No. GB 1196/1904, which is hereby incorporated by reference. A further analysis of the Scheimpflug geometry is found at http://www.trenholm.org/hmmerk/SHSPAT.pdf. Adjustable polarizer 325 is positioned between sample 305 and detector 315. The angle of detection was adjusted to be the Brewster angle for silicon, i.e., the angle for which the reflectivity of p-polarized incident light goes to zero. At the Brewster angle in P polarization, the wafer "goes dark" and it becomes much easier to see small signal changes.

Figure 4:
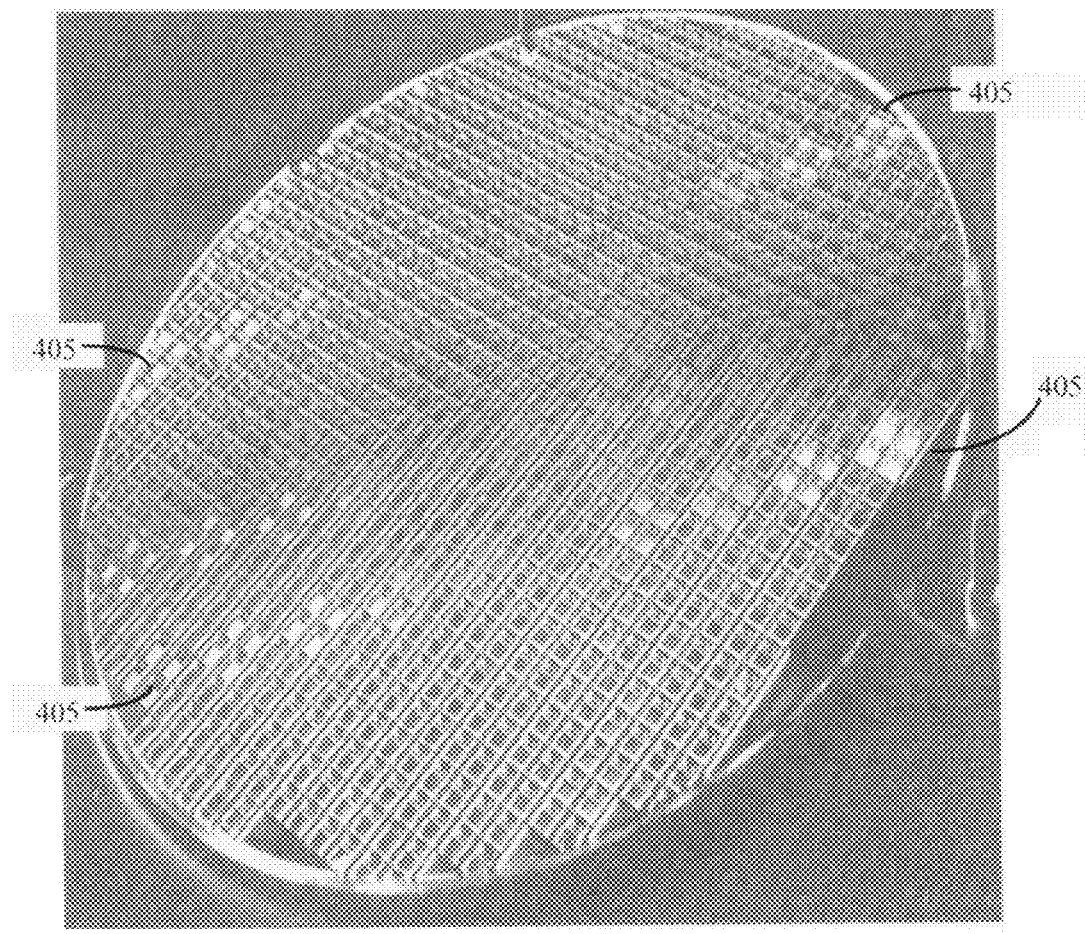
FIG. 4 shows an image of a test wafer using oblique incidence illumination, oblique detection, and P polarization.

Under these conditions, a test wafer was imaged using P polarization. The wafer contained diagonal rows of variable focus and variable exposure dies. The wafer image was subtracted from that of a wafer without the anomalies, and was rescaled, stretched in y and re-contrasted for illustration purposes. The resultant image is shown in FIG. 4. The diagonal lines 405 clearly show the focus/exposure effects. Color variation was also seen which gives a "direct readout" of the defocus or exposure variation. The image could be improved further by using a microscope setup to image the resist pattern in at least 2 points, and rotating and translating the wafer to accurately register the pattern itself. If this process is followed, the bright edges remaining in the image of FIG. 4 would largely vanish, leaving mainly only the defects of interest. One problem with this configuration is the lack of telecentricity of the imaging lens, which results in a top/down and left/right variation of base intensities.

Figure 5:
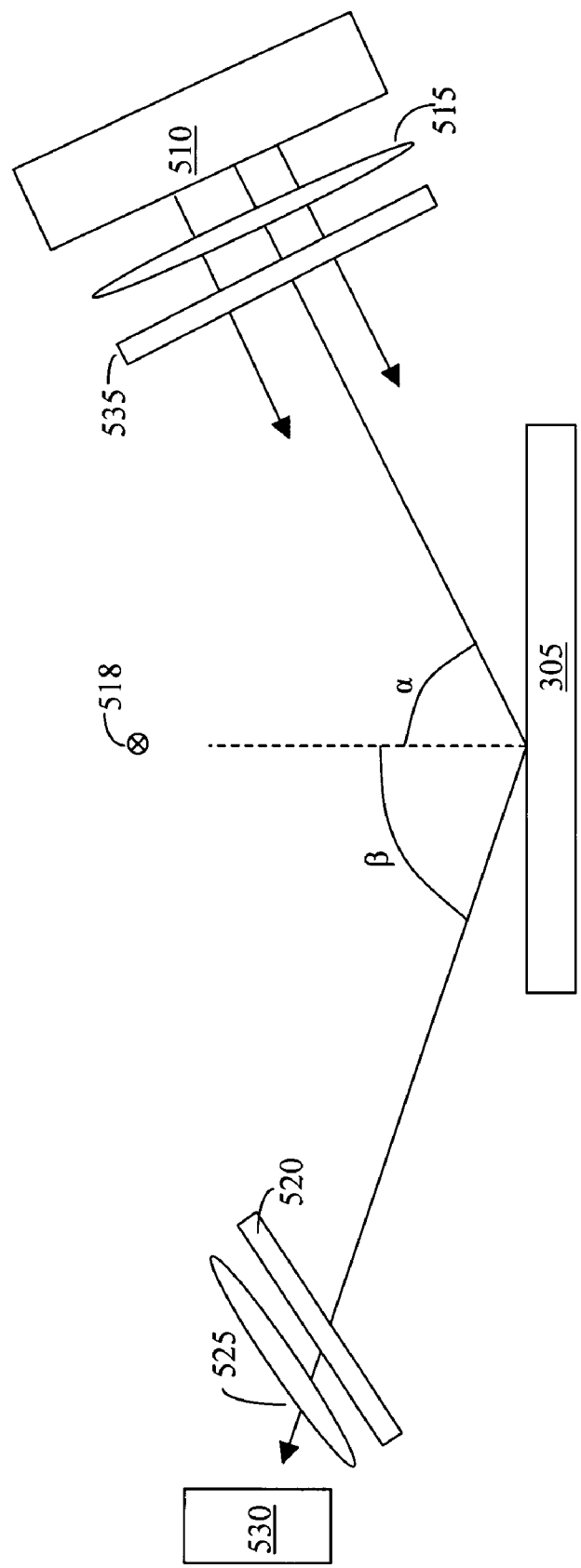
FIG. 5 shows an embodiment of the invention using a configuration similar to that of FIG. 4 which can be incorporated into the architecture of a line-scan macro-inspection system.

In an embodiment of the present invention, a configuration similar to that of FIG. 3 is implemented which can be incorporated into the architecture of a line-scan macro-inspection system such as the Viper system made by KLA-Tencor, with a broad variation in angles of incidence and detection. This embodiment is illustrated in FIG. 5. Wafer 505 is oriented perpendicular to the plane of the paper. Illuminator 510 is a fiber-optic light line with fanned fibers, and collimating illumination optics 515 are placed in front of illuminator 510 to provide telecentricity perpendicular to the scan direction, which is into the plane of the paper. Analyzer 520 and imaging optics 525 are positioned between sample 505 and line-scan sensor 530. The sensor and imaging optics are oriented to the sample according to the Schiempflug geometry so as to keep the entire sample in focus. Note that the dimension of the imaging and illumination optics may be smaller than the 300 nm wafer diameter due to the oblique angle of observation. The imaging and illumination optics may be curved mirrors, by way of example. Polarizer 535 may be positioned on the illumination side to permit cross-polarization observation. The configuration as shown is effectively a one-dimensional imaging ellipsometer. The analyzer could be replaced with a polarizing beam splitter splitting the line image onto two line sensors, each observing with a different polarization. Alternatively, dichroic beam splitters could split the images into more sensors so as to provide spectral information, as follows: Dichroic beam splitters allow transmission of wavelengths above a critical wavelength, and reflects those below. Using a dichroic beam splitter, the outgoing light from the sample can be split by wavelength, therefore separate measurements can be made on each wavelength range. Alternately, a 2D sensor having a grating or prism could be used to spread light be wavelength into multiple adjacent lines.

Figure 6:
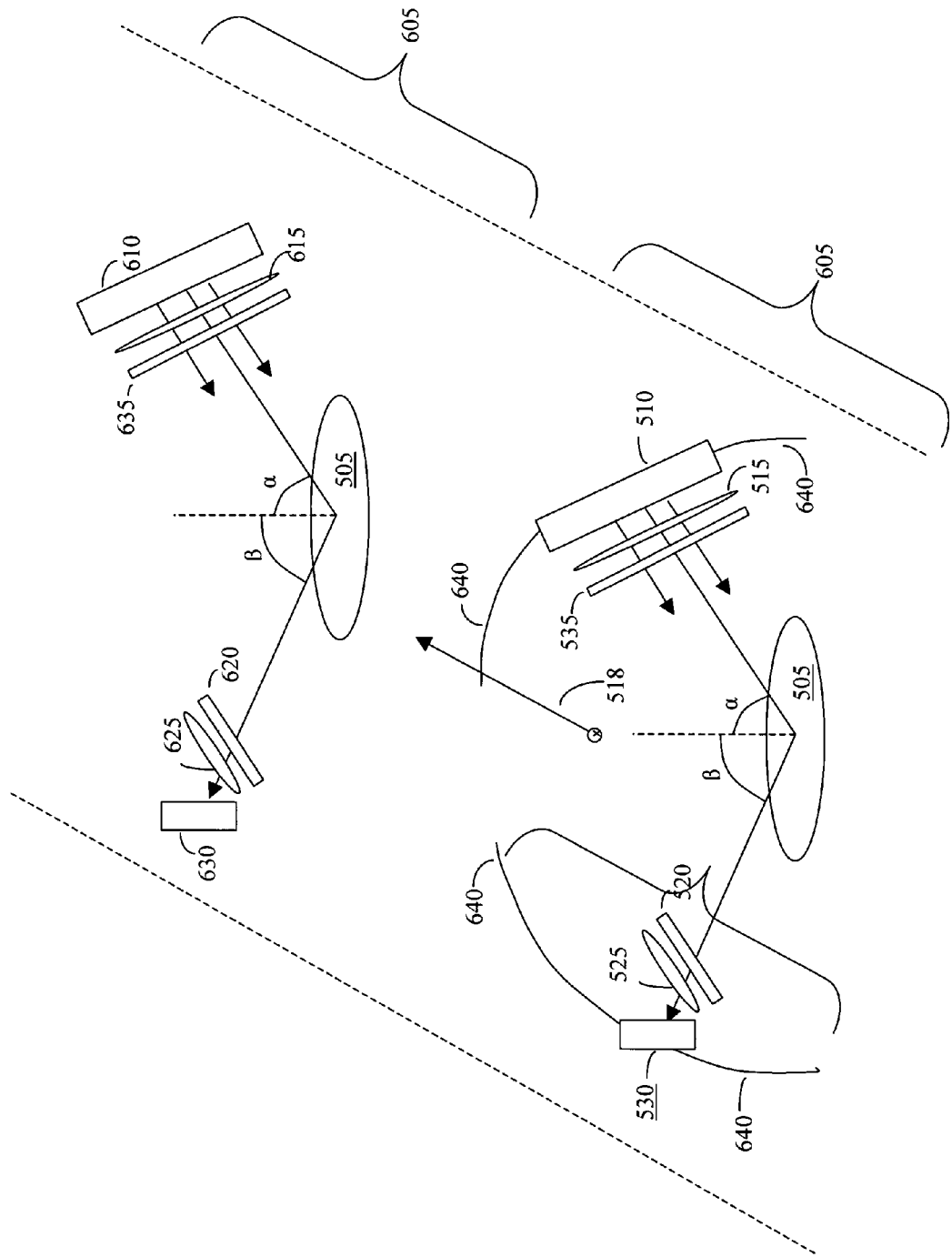
FIG. 6 is an illustration of an embodiment of the invention employing multiple stages as in FIG. 5.

Because of the scan direction 518 with respect to the illumination and optics, the geometry resembles a car wash whereby the wafer may pass sequentially through multiple stages (with a single stage as shown in FIG. 5), with multiple illuminators 510, 610, and multiple analyzers 520, 620. FIG. 6 is an illustration of another embodiment of the invention. For example, laser line generators can be used, and each stage 605 could utilize a different wavelength of illumination. Alternatively or additionally, different polarizations could be analyzed, and different angles of incidence of illumination could be employed. The configuration, with both the illuminators and the detectors moved to the side so as not to interfere with the scan motor, also gives sufficient space to facilitate the broad tuning of the angle of incidence and angle of detection. This tuning could be accomplished by mounting the illuminator 510 and sensor 530 on circular rails 640, allowing the selection of illumination and/or observation angles. The illuminators or detectors could be moved in a motorized fashion using lead screws, rack-and-pinion mechanisms, or piezomotors. Whereas the available space is limited for any one position along the scan direction, by adding the capability of arranging illuminators, analyzer, and sensors at varying positions along the scan direction, a great deal of potential space is made available.

Figure 7:
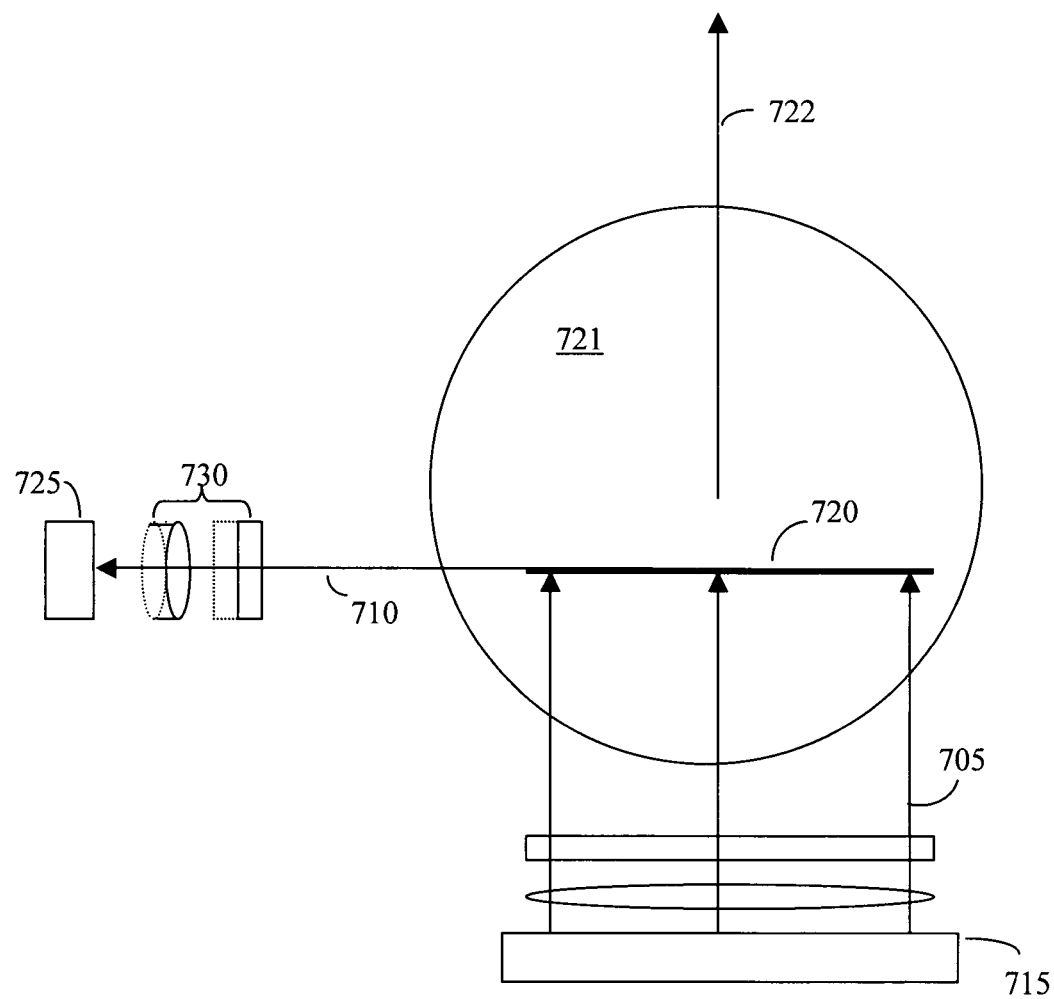
FIG. 7 illustrates an embodiment of the invention which incorporates double darkfield analysis into the Viper line scan architecture.

Another embodiment, with one possible configuration illustrated in FIG. 7, incorporates double darkfield analysis into the Viper line scan architecture. If the incident illumination vector 705 is not coplanar with the outgoing light vector 710 entering the analyzer and sensor, scattering in two directions has occurred before detection, resulting in very low background signal. As illustrated in the figure from a top view, illuminator 715 which may be a fiber optic fan illuminates a line 720 across the wafer 721 which is scanning in direction of arrow 722. A possible illuminator configuration is described by commonly owned U.S. Pat. No. 6,796,697 (shown in FIG. 4), which is hereby incorporated by reference. Line sensor 725 employs Scheimpflug optics 730. Note that the illuminator and detector positions could be exchanged, using a conventional line sensor imager as a camera.

The inventive embodiments as described above can be added to an existing Viper macro-inspection system as an additional acquisition channel. The pixel size in the scan direction (defined as the x-direction) is given by the sampling rate of the sensor, and can be small, consistent with the current Viper configuration. The resolution in the direction perpendicular to the scan, but parallel to the sample surface (defined as the y-direction) will be reduced by the oblique detection angle. The line scan configuration disclosed herein can be implemented using standard Viper components, i.e., sensors and illuminators, thus potentially yielding a short time-to-market. The system as described is modular and can be kept almost completely independent of the existing Viper system, thereby easing the software development effort.

It is not intended that the invention be restricted to the exact embodiments disclosed herein. It should be apparent to one skilled in the art that certain changes and modifications can be made without departing from the inventive concept. For example, other types of analyzers may be incorporated in additional stages, such as: point measuring sensors, 2D sensors, 2D sensors with gratings in front for multispectral observations. Other types of illuminators may be used, such as short laser-line generators for monochromatic observations. The scope of the invention should be construed in view of the claims.

With this in mind, I claim:

1. An image acquisition apparatus stage for scanning a sample in a scan direction, said apparatus stage comprising:
an illumination source arranged to direct an incident illumination beam onto an illumination spot on the surface of said sample at a first angle relative to said sample surface, said first angle being broadly tunable to varying oblique angles; and
at least one sensor for detecting light from said illumination source scattered off of said sample surface at a second angle relative to said sample surface, said second angle being broadly tunable to varying oblique angles, said detected light forming a scattered beam;
said image acquisition apparatus stage suitable for being added onto a wafer macro-inspection system.

2. The image acquisition apparatus stage of claim 1, wherein said image acquisition stage is a line image acquisition apparatus stage suitable for being added onto a line-scan wafer macro-inspection system, and wherein said at least one sensor is at least one line sensor.

3. The line image acquisition apparatus stage of claim 2, wherein said incident illumination beam and said scattered beam are coplanar.

4. The line image acquisition apparatus stage of claim 2, wherein said incident illumination beam and said scattered beam are not coplanar, said line sensor thereby performing double darkfield detection.

5. The line image acquisition apparatus stage of claim 2, further comprising an analyzer for analyzing light from said illumination source scattered off of said sample surface, said analyzer positioned between said sample surface and said at least one line sensor.

6. The line image acquisition apparatus stage of claim 5, wherein said incident illumination beam and said scattered beam are not coplanar, said line sensor thereby performing double darkfield detection.

7. The line image acquisition apparatus stage of claim 6, wherein said incident illumination beam is coplanar with said scan direction, and wherein said scattered beam is perpendicular to said scan direction.

8. The apparatus stage of claim 5, further comprising imaging optics positioned between said sample and said at least one line sensor, said imaging optics sending a line image to be detected by said at least one line sensor.

9. The apparatus stage of claim 8, wherein said at least one line sensor and said imaging optics are oriented to said sample surface according to Scheimpflug geometry, thereby keeping the entire said sample surface in focus.

10. The apparatus stage of claim 8, wherein said analyzer splits said line image into a plurality of split line images, each said split line image being directed onto a different one of said at least one line sensors.

11. The apparatus stage of claim 10, wherein said analyzer splits said line image into discrete wavelength ranges.

12. The apparatus stage of claim 11, wherein said analyzer is one of: a dichroic beam splitter, and a 2D sensor having one of a grating and a prism.

13. The apparatus stage of claim 2, wherein said illumination source is a line illumination source.

14. The apparatus stage of claim 2, wherein said illumination source is a fiber-optic line with fanned fibers.

15. The apparatus stage of claim 2, further including collimating optics positioned between said illumination source and said sample surface to provide telecentricity perpendicular to said scan direction.

16. The apparatus stage of claim 2, further including a polarizer positioned between said illumination source and said sample surface.

17. The line image acquisition apparatus stage of claim 2, wherein said incident illumination beam and said scattered beam are coplanar in an xy plane, and wherein said sample scan direction is a z-direction.

18. The line image acquisition apparatus stage of claim 2, wherein at least one of said incident illumination beam and said scattered beam is out of an xy plane, said incident illumination beam and said scattered beam are not coplanar, and wherein said sample scan direction is a z-direction.

19. The line image acquisition apparatus stage of claim 18, further comprising an analyzer for analyzing light from said illumination source scattered off of said sample surface, said analyzer positioned between said sample surface and said at least one line sensor, said analyzer thereby providing double darkfield analysis.

20. The apparatus stage of claim 19, wherein said analyzer is a polarizing beam splitter to split said line image onto two polarization line sensors such that each said polarization line sensor observes light with a different polarization.

21. The apparatus stage of claim 2, wherein said second angle is the Brewster angle of said sample.

22. The apparatus stage of claim 2, wherein said illuminator and said detector are mounted on a curved mounting, and further including a means for tuning at least one of said first angle and said second angle, by moving at least one of said illuminator and said detector, said means comprising one selected from the set consisting of: lead screws, rack-and-pinion mechanisms, and piezomotors.

23. A line image acquisition apparatus, said apparatus suitable for being added onto a line-scan wafer macro-inspection system for scanning a sample in a scan direction, said apparatus comprising a plurality of line image acquisition apparatus stages as in claim 2.

24. The line image acquisition apparatus of claim 23, wherein for at least one of said plurality of line image acquisition apparatus stages said incident illumination beam and said scattered beam are not coplanar, said line sensor thereby performing double darkfield detection.

25. The line image acquisition apparatus of claim 24, wherein said plurality of line image acquisition stages are disposed along the z-direction, whereby said sample passes through each of said line image acquisition stages as it scans in the z-direction.

26. The apparatus of claim 25, wherein the illumination source for each said line image acquisition stage provides a unique wavelength of illumination relative to other said line image acquisition stages.

27. The apparatus of claim 25, wherein each said line acquisition stage has a unique said first angle relative to other said line image acquisition stages.

28. The apparatus of claim 25, wherein each said line acquisition stage analyzes a unique polarization relative to other said line image acquisition stages.

29. A line image acquisition apparatus for scanning a sample in a scan direction;
said apparatus suitable for being added onto a line-scan wafer macro-inspection system,
said apparatus comprising a plurality of line image acquisition apparatus stages as in claim 2, wherein for at least one of said line image acquisition stages at least one of said incident illumination beam and said scattered beam is out of an xy plane, said incident illumination beam and said scattered beam are not coplanar, and wherein said sample scan direction is a z-direction, and wherein said at least one of said line image acquisition stages further comprises an analyzer for analyzing light from said illumination source scattered off of said sample surface, said analyzer positioned between said sample surface and said at least one line sensor, said analyzer thereby providing double darkfield analysis.

30. The apparatus stage of claim 1,
further comprising an analyzer for analyzing light from said illumination source scattered off of said sample surface, said analyzer positioned between said sample surface and said at least one sensor;
further comprising imaging optics positioned between said sample and said at least one sensor, said imaging optics sending an image to be detected by said at least one sensor; and
wherein said at least one sensor and said imaging optics are oriented to said sample surface according to Scheimpflug geometry, thereby keeping the entire said sample surface in focus.

31. The apparatus stage of claim 30, wherein said at least one sensor is a 2D sensor.

32. An image acquisition apparatus, said apparatus suitable for being added onto a wafer macro-inspection system for scanning a sample in a scan direction, said apparatus comprising a plurality of image acquisition apparatus stages as in claim 1.

33. The image acquisition apparatus of claim 32, wherein for at least one of said plurality of image acquisition apparatus stages said incident illumination beam and said scattered beam are not coplanar, said sensor thereby performing double darkfield detection.

34. The image acquisition apparatus of claim 32, wherein at least one of said plurality of image acquisition apparatus stages includes one selected from the group consisting of: a 2D sensor, a 2D sensor with gratings in front for multispectral observations, a point measuring sensor, and a short laser-line generator illuminator for monochromatic observations.

* * * * *